US00PP08717P

United States Patent [19]

De Meyer

[11] Patent Number: Plant 8,717

[45] Date of Patent: May 3, 1994

[54] GUZMANIA PLANT NAMED TUTTI FRUTTI

[75] Inventor: Henri De Meyer, Destelbergen, Belgium

[73] Assignee: H. De Meyer-De Rouck, Laarne, Belgium

[21] Appl. No.: 75,274

[22] Filed: Jun. 11, 1993

[51] Int. Cl.[5] ..... A01H 5/00

[52] U.S. Cl. ..... Plt./88.8

[58] Field of Search ..... Plt. 88.8

*Primary Examiner*—James R. Feyrer

*Attorney, Agent, or Firm*—Foley & Lardner

[57] ABSTRACT

A new and distinct cultivar of Guzmania plant named Tutti Frutti, characterized by the combined features of multi-colored bracts, with the top bracts varying from green at the sheaths over orange and red, to a black tip. The bottom bracts have a green tip and a red lower half. The completely green leaf sheaths are well formed when fully grown and are closely linked at the base. The inflorescence lasts over six months.

2 Drawing Sheets

The present invention comprises a new and distinct cultivar of *Guzmania squarrosa,* referred to by the cultivar name Tutti Frutti. The genus Guzmania is within the family Bromeliaceae.

Tutti Frutti is a product of a planned breeding program conducted in Laarne, Belgium. The program evolved from the importation by the inventor of seeds of several different cultivars of *Guzmania squarrosa* from Ecuador. When grown out to flower, several plants were selected for their beautiful flowers, and were subsequently crossed with cultivars of the species *Guzmania minor.*

Tutti Frutti was originated by the inventor from a hybridization made in the program in Laarne, Belgium. The female parent was an unnamed *Guzmania minor* species identified as "red". The male parent of Tutti Frutti was an unnamed variety of *Guzmania squarrosa.*

Tutti Frutti was discovered and selected by the inventor after flowering in early 1989. The new cultivar was thereafter asexually reproduced from offshoots under the supervision of the inventor in a controlled environment in Laarne, Belgium. The offshoots were rooted, with the resulting plantlets being detached from the mother plant and potted up in an appropriate growing mixture.

Horticultural examination of plants so propagated has demonstrated that the combination of characteristics as herein disclosed for Tutti Frutti are firmly fixed and retained through successive generations of asexual reproduction, which can be effected by offshoots as described, or by known tissue culture techniques. The new cultivar cannot be propagated from its own seed.

Tutti Frutti has not been observed under all possible environmental conditions. The phenotype may vary significantly when grown under different conditions of temperature, light, and other determining factors, without, however, any variation in genotype. The following observations, measurements and comparisons describe plants grown in Laarne, Belgium under greenhouse conditions which approximate those generally used in commercial practice.

The following traits have been repeatedly observed and are determined to be basic characteristics of Tutti Frutti which in combination distinguish this Guzmania as a new and distinct cultivar:

1. Tutti Frutti has multi-color bracts. The upper bracts vary from green at the sheaths over orange and red, to a black tip. The bottom bracts have a green tip and a red colored lower half.

2. The lower leaves are primarily dark green in color and provide excellent contrast with the sturdy flower cone.

3. The inflorescence is long lasting (over six months).

4. The fully grown leaf sheaths are well formed and closely linked at the base. The leaf sheaths are completely green.

The accompanying color photographic drawings show the inflorescence and foliage characteristics of Tutti Frutti as clearly as possible.

The photo on the first sheet comprises a top perspective view of a substantial part of a plant of Tutti Frutti in bloom.

The photo on the second sheet comprises a top view showing the inflorescence in much greater detail. The colors are as nearly true as possible with illustrations of this type.

Tutti Frutti can be compared in certain respects to the commercially available Guzmania cultivar Denise. For comparably grown plants, Tutti Frutti is bigger than Denise, and Tutti Frutti is further distinguished from Denise by its larger flowers and multi-color bracts.

In the following description, color references are made to the Royal Horticultural Society Colour Chart. The color values were determiend at Laarne, Belgium.

Classification:

*Botanical.*—*Guzmania minor*×*squarrosa,* cv. Tutti Frutti.

PLANT

Form: Rosette.

Height: About 50 cm when plant is in bloom. The leaf rosette has a height of about 35 cm.

Diameter: Approximately 85–100 cm when plant is in bloom.

Growth habit: Stemless.

Method of propagation: By offshoots or tissue culture.

Foliage:

*Quantity.*—Some 28 to 30 leaves form a close rosette.

*Size.*—The fully grown leaves have a width of about 5 cm and a length of 60 cm.

*Shape.*—Linear with a pointed tip.

*Surface texture.*—The leaf surface is ribbed and shiny, both top and bottom surfaces.

*Color.*—The top surface is approximately 147A and the bottom surface is approximately 147B.

*Leaf sheaths.*—Well formed and closely linked at the base, having a length of 9–14 cm up to the narrowing, and a width of 8–10 cm. The newest leaves (in the center of the rosette) bear a fine purple striped pattern.

BRACTS

Quantity: Some 28 bracts are regularly spread along the length of and completely surround the flower shaft.

Size: Bracts at the bottom of the flower shaft have a length of about 40 cm and a width of 5.5 cm; bracts near the top of the flower shaft have a length of 10 to 20 cm and a width of 7 cm at the base.

Shape: At approximately one-third of the length from the top of the bracts, the leaf blade curls outwards.

Color: The bracts of the lower half of the flower vary in color from the green sheaths (152B) over a fire red color (33B), to a cherry red (45C), and ending in a brown black tip (200A), whereas the top bracts vary from the green leaf sheaths (152C) to a fire red color (33B).

FLOWERS

Borne: Some 9 to 11 headlike subflower systems are embedded, each separately, in the axils of one of the top bracts. Individual flowers cling to a fibrous receptacle.

Blooming habit: Flowers bloom approximately 16 weeks after induction. Single flowers bloom only one day, and the total inflorescence (from the first to last flower) lasts approximately twelve (12) weeks.

Quantity: About 16 to 21 single flowers in each subflower system.

Size: The entire flower system (all subflowers together), which is part of the inflorescence, has a length of approximately 13 cm and a diameter of 8 cm. Each subflower system typically has a length of 4.5 cm and a width of 3 cm. Each individual flower is about 4.5 to 5 cm in length.

Shape: Straight in the subflower system.

Color: The bract of each flower has a fine striped red transparent color at the top half (41B) and a transparent white (150B) at the bottom.

Sepals: Three in number, fasciated at the base and membranous (4D). Sepals have a length of approximately 2 cm and a width of approximately 3 mm.

Petals: There are three in number, fasciated with each other and with the 6 stamens. The petals have a length of approximately 2.5 cm and a width of approximately 4 mm. Petal color is 9A.

Seed capsule: A reddish brown pyxidium of about 3 cm is formed.

Reproductive organs: There is one pistil and 6 stamens; typical in shape and color.

I claim:

1. A new and distinct cultivar of Guzmania plant named Tutti Frutti, as illustrated and described.

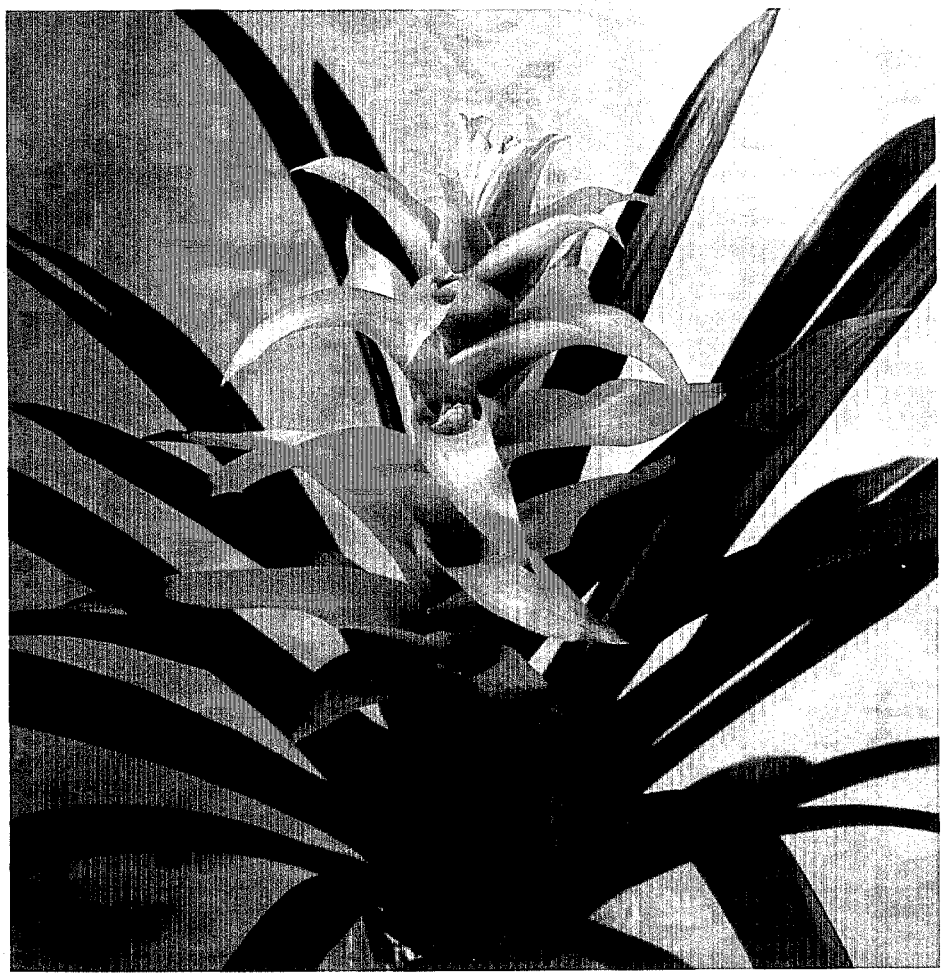

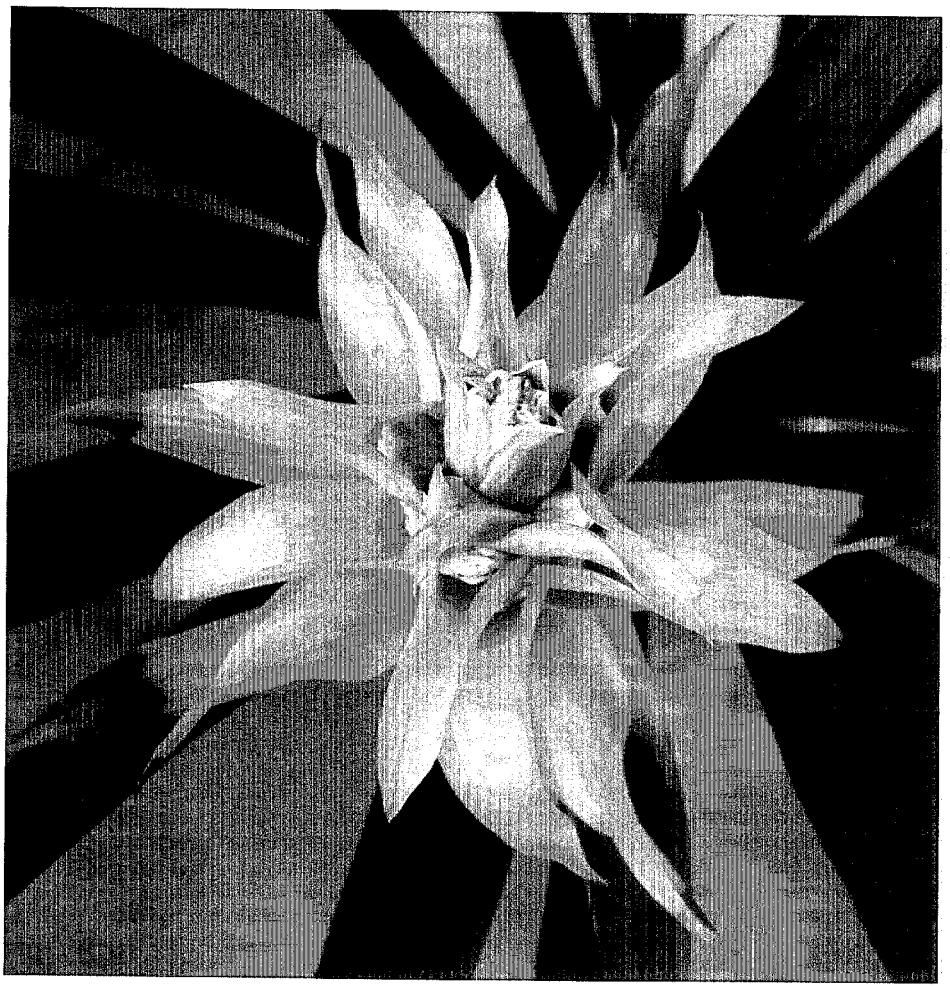

* * * * *